(12) United States Patent
Polic et al.

(10) Patent No.: US 12,168,136 B2
(45) Date of Patent: Dec. 17, 2024

(54) DISTRIBUTED DEFIBRILLATOR SYSTEM TO ENABLE RAPID RESPONSE FOR CARDIAC OR PULMONARY ARREST

(71) Applicants: Vladimir Polic, Portoroz (SI); Martin Alpert, Beachwood, OH (US)

(72) Inventors: Vladimir Polic, Portoroz (SI); Martin Alpert, Beachwood, OH (US)

( * ) Notice: Subject to any disclaimer, the term of this patent is extended or adjusted under 35 U.S.C. 154(b) by 0 days.

(21) Appl. No.: 17/373,997

(22) Filed: Jul. 13, 2021

(65) Prior Publication Data
US 2022/0314009 A1    Oct. 6, 2022

Related U.S. Application Data

(60) Provisional application No. 63/168,709, filed on Mar. 31, 2021.

(51) Int. Cl.
*A61N 1/39* (2006.01)
*G08B 5/22* (2006.01)
*G08B 25/10* (2006.01)

(52) U.S. Cl.
CPC ......... *A61N 1/3904* (2017.08); *A61N 1/3925* (2013.01); *A61N 1/3968* (2013.01);
(Continued)

(58) Field of Classification Search
CPC .................................................. A61N 1/3968
See application file for complete search history.

(56) References Cited

U.S. PATENT DOCUMENTS 5,741,306 A * 4/1998 Glegyak .............. A61N 1/3904
607/12
5,873,899 A * 2/1999 Stutz, Jr. ............ A61N 1/37512
607/36
(Continued)

FOREIGN PATENT DOCUMENTS

WO   WO-2015017725 A1 * 2/2015 ............... A61N 1/39
WO      2020000098 A1    1/2020
WO      2021007588 A1    1/2021

OTHER PUBLICATIONS

International Search Report and Written Opinion corresponding to counterpart International Patent Application PCT/US2022/022534 mailed Oct. 24, 2022.

*Primary Examiner* — Eric D. Bertram
(74) *Attorney, Agent, or Firm* — Renner, Otto, Boisselle & Sklar, LLP

(57) ABSTRACT

A portable wearable defibrillator device, a distributed defibrillator system, and a computer-implemented method use at least one node that is connected to a wireless network and communicates with sensors, electronic mobile devices, and/or defibrillator devices to determine when a person is having a cardiac or pulmonary event or other event, identify a person who is able to assist the arresting person, and notify the assisting person and/or any other emergency contacts and/or emergency personnel. The electronic components of the wearable defibrillator are arranged in serial to minimize the size of the defibrillator. The control circuit of the wearable defibrillator is configured to provide fast charging for the capacitor, such that the defibrillator is able to be used at any time and frequently. An application for an electronic mobile device is used to interface with an assisting person and other people, e.g., emergency contacts or emergency personnel, associated with the network.

11 Claims, 6 Drawing Sheets

(52) U.S. Cl.
CPC ......... *A61N 1/3975* (2013.01); *A61N 1/3993* (2013.01); *G08B 5/22* (2013.01); *G08B 25/10* (2013.01)

(56) References Cited

U.S. PATENT DOCUMENTS

| | | | |
|---|---|---|---|
| 6,148,233 A | 11/2000 | Owen et al. | |
| 10,092,767 B1* | 10/2018 | Newton | A61N 1/3925 |
| 2004/0143297 A1* | 7/2004 | Ramsey, III | A61N 1/3975 |
| | | | 607/5 |
| 2009/0306730 A1* | 12/2009 | Roso | A61N 1/3968 |
| | | | 607/5 |
| 2010/0241181 A1* | 9/2010 | Savage | A61N 1/3968 |
| | | | 607/5 |
| 2012/0010543 A1* | 1/2012 | Johnson | G16H 20/40 |
| | | | 601/41 |
| 2012/0011382 A1* | 1/2012 | Volpe | A61N 1/08 |
| | | | 713/323 |
| 2015/0039039 A1* | 2/2015 | Macho | H01L 23/5387 |
| | | | 29/832 |
| 2015/0196867 A1* | 7/2015 | Ries | H01M 10/4264 |
| | | | 429/57 |
| 2015/0257709 A1* | 9/2015 | Quan | A61B 5/7257 |
| | | | 600/510 |
| 2015/0321022 A1* | 11/2015 | Sullivan | A61N 1/046 |
| | | | 607/5 |
| 2016/0100302 A1 | 4/2016 | Barash et al. | |
| 2016/0271408 A1* | 9/2016 | Newton | A61N 1/3904 |
| 2018/0140859 A1* | 5/2018 | Meir | A61N 1/3981 |
| 2018/0169426 A1* | 6/2018 | Montague | A61N 1/3981 |
| 2018/0207435 A1* | 7/2018 | Yetter | A61N 1/3925 |
| 2018/0221645 A1 | 8/2018 | Medema et al. | |
| 2019/0022400 A1* | 1/2019 | Kumar | A61N 1/3904 |
| 2019/0117989 A1* | 4/2019 | Andrews | H01R 33/74 |
| 2019/0143131 A1* | 5/2019 | Webster | A61N 1/3925 |
| | | | 607/7 |
| 2019/0192867 A1* | 6/2019 | Savage | A61N 1/3925 |
| 2019/0255341 A1* | 8/2019 | Buchanan | A61N 1/3975 |
| 2019/0329056 A1* | 10/2019 | Sjoquist | A61N 1/3987 |
| 2019/0329057 A1* | 10/2019 | Teber | A61N 1/046 |
| 2020/0078597 A1* | 3/2020 | Henschel | A61N 1/3758 |
| 2020/0373005 A1 | 11/2020 | Halsne et al. | |

* cited by examiner

DISTRIBUTED DEFIBRILLATOR SYSTEM TO ENABLE RAPID RESPONSE FOR CARDIAC OR PULMONARY ARREST

RELATED APPLICATIONS

This application claims the benefit of U.S. Provisional Application No. 63/168,709 filed Mar. 31, 2021, which is hereby incorporated herein by reference in its entirety.

FIELD OF DISCLOSURE

The present application relates to a distributed defibrillator system, a wearable defibrillator device, and an optional computer-implemented method that uses a wireless network to communicate with users who have access to portable defibrillators for rapidly responding to a cardiac or pulmonary arrest.

BACKGROUND

When a person has a cardiac or pulmonary arrest, the arresting person is not be able to defibrillate themselves even if they have a defibrillator nearby. For example, the person may be sleeping or otherwise incapacitated. Thus, another person who is able to defibrillate the arresting person must be notified in a timely manner such that the assisting person is able to reach the arresting person quickly. Conventional defibrillator systems and methods are deficient in that someone who is able to assist an arresting person may not be notified in a timely manner, such that the arresting person may not receive immediate defibrillation and resuscitation.

SUMMARY OF DISCLOSURE

The present application provides a portable wearable defibrillator device, a distributed defibrillator system, and a computer-implemented method for the distributed defibrillator system. The distributed defibrillator system may include at least one node that is connected to a wireless network and is configured to communicate with sensors, electronic mobile devices, and/or defibrillator devices themselves to determine when a person is having a cardiac or pulmonary event, identify a person who is able to assist the arresting person, and notify the assisting person and/or any other emergency contacts and/or emergency personnel. The computer-implemented method may include a mobile device application which may be accessed by any person who witnesses an arrest, regardless of whether the person is able to assist the arresting person, such that the mobile device application may be used to identify another person who is able to assist. The distributed defibrillator system ensures that an appropriate person is notified in a timely manner to assist the arresting person. In an embodiment, a person who is wearing the wearable defibrillator and witnesses an arrest, may use the wearable defibrillator to defibrillate the arresting person without going through a network.

The electronic components of the portable wearable defibrillator device are configured to minimize size and are arranged in a serial arrangement which enables the size of the defibrillator to be minimized as compared with conventional defibrillators. For example, the defibrillator may be similar in size to a cell phone. The control circuit of the wearable defibrillator is configured to provide fast charging for the capacitor of the defibrillator, such that the defibrillator is able to be used at any time and reused more frequently than conventional defibrillators. Accordingly, more shocks can be performed in less time. The wearable defibrillator may be configured to be used with the distributed defibrillator system network. The computer-implemented method may also be downloadable as an application for an electronic mobile device that is configured to connect to the distributed defibrillator system network. Instructions for use of the defibrillator may be provided through the defibrillator system, or through any interface between the defibrillator and a mobile device. The application may be used to interface with the assisting person and other people, e.g., emergency contacts or emergency personnel, associated with the network. Any suitable communication protocol may be used.

Approximately 70% of cardiac arrests that occur can be converted, resuscitating the person. If this is done within the first five minutes of the arrest, there is typically no residual deficit in the person. However, the average time for an emergency personnel to reach the arresting person and resuscitate is approximately 11 minutes. Using the devices, systems, and methods described herein, the average time may be reduced to within five minutes. Given that cardiac arrests kill a large number of people, the devices, systems, and methods described herein may save more lives and also maintain a quality of life as compared with other therapies or prior attempts to improve defibrillation device, systems, and methods.

According to an aspect of the disclosure, the distributed emergency defibrillator system includes at least one node that is configured to, in response to an input that a person is having a cardiac or pulmonary event, determine a first location where the cardiac or pulmonary event is occurring based on location information associated with the input, communicate with a wireless network to determine at least one of mobile electronic devices associated with users who have access to portable defibrillator units, and send a notification to the at least one of the mobile electronic devices indicating that the cardiac or pulmonary event is occurring at the first location.

According to an aspect of the disclosure, a distributed defibrillator system uses at least one node via which to notify people who have access to portable defibrillators that a person is having a cardiac or pulmonary event.

According to an aspect of the disclosure, a wearable defibrillator is arranged to be compact and fast-charging. The fast charging permits more defibrillations in less time.

According to an aspect of the disclosure, a computer-implemented method is executed by at least one node via which to send notifications to mobile devices that a cardiac or pulmonary event is occurring and where the event is occurring.

According to an aspect of the disclosure, since many people may be wearing the defibrillator all the time, including police, fireman, emergency medical service (EMS) personnel, and private citizens, the wearers may be close to someone that needs defibrillation and directly implement defibrillation without going through the network.

According to an aspect of the disclosure, a distributed emergency defibrillator system includes at least one node configured to, in response to an input that a person is having a cardiac or pulmonary event, determine a location where the cardiac or pulmonary event is occurring based on location information associated with the input, communicate with a wireless network to determine at least one of mobile electronic devices associated with users who have access to portable defibrillator units, and send a notification to the at least one of the mobile electronic devices indicating that the cardiac or pulmonary event is occurring at the location.

According to an embodiment of any paragraph(s) of this summary, the notification may include an alarm configured to output a unique sound or audio verbal signal for each of a cardiac event and a pulmonary event.

According to an embodiment of any paragraph(s) of this summary, the at least one node may be configured to store data pertaining to emergency contacts who are associated with the person located within the proximity of the at least one sensor and who are also associated with secondary mobile electronic devices other than the mobile electronic devices associated with the users who have access to the portable defibrillator units, and send a secondary notification to at least one of the secondary mobile electronic devices indicating that the cardiac or pulmonary event is occurring.

According to an embodiment of any paragraph(s) of this summary, the at least one node may be configured to receive the input from at least one sensor.

According to an embodiment of any paragraph(s) of this summary, the at least one node may be configured to receive the input from the at least one sensor that is arranged in one of the portable defibrillator units.

According to an embodiment of any paragraph(s) of this summary, the at least one node may be configured to receive the input from the at least one sensor that is integrated into or in proximity to a bed, a mattress, a pillow, or integrated into an alarm clock, or a wearable device, wherein the at least one sensor is configured to monitor the person located within the proximity of the at least one sensor while the person is sleeping.

According to an embodiment of any paragraph(s) of this summary, the at least one node may be configured to receive the input from the at least one sensor that is integrated into a personal mobile electronic device associated with the person having the cardiac or pulmonary event.

According to an embodiment of any paragraph(s) of this summary, the at least one node may be configured to send a signal to another node, the signal indicating that the cardiac or pulmonary event is occurring.

According to an embodiment of any paragraph(s) of this summary, the at least one node may be configured to send a secondary notification to a central call station for emergency response.

According to an embodiment of any paragraph(s) of this summary, the at least one node may be located at a central call station.

According to an embodiment of any paragraph(s) of this summary, the at least one node may be configured to store data pertaining to authorized users who are associated with the mobile electronic devices and who are authorized to access lock boxes containing the portable defibrillator units, and send an access code for at least one of the lock boxes to the at least one of the mobile electronic devices that is associated with one of the authorized users, or automatically unlock the at least one of the lock boxes.

According to an embodiment of any paragraph(s) of this summary, the at least one node may be configured to receive the input from at least one of a pO2 sensor, a pcO2 sensor, a movement transducer, an electrocardiogram transducer, a heart mechanical activity sensor, or a heart electrical activity sensor.

According to an embodiment of any paragraph(s) of this summary, the at least one node may be a server.

According to another aspect of the disclosure, a wearable defibrillator includes a capacitor, a battery, control circuitry, power circuitry, separable pads having electrodes, and a discharge circuit electrically coupled with the control circuitry and configured to release a voltage from the capacitor to at least one of the electrodes, wherein the capacitor, the battery, and the power circuitry are arranged in serial with stacked discharge and control boards.

According to an embodiment of any paragraph(s) of this summary, the wearable defibrillator may include a disconnectable mount for mounting the wearable defibrillator to a person.

According to an embodiment of any paragraph(s) of this summary, the wearable defibrillator may include a disconnectable mount for mounting the separable pads to a person.

According to an embodiment of any paragraph(s) of this summary, the wearable defibrillator may include a self-test module, wherein the self-test module monitors battery strength and functionality of the wearable defibrillator.

According to an embodiment of any paragraph(s) of this summary, the capacitor may be a rechargeable capacitor and/or is configured to be charged at a maximum rate until the capacitor is nearly at full charge at which the capacitor is then charged at a decreased rate.

According to an embodiment of any paragraph(s) of this summary, the wearable defibrillator may include a display and a communication protocol of the wearable defibrillator may be normally in a sleep mode and configured to automatically switch into an on mode when the display is touched for a predetermined period of time or in response to detection of the cardiac or pulmonary event occurring in the person.

According to an embodiment of any paragraph(s) of this summary, the wearable defibrillator may include a single continuous casing in which the control circuitry, the power circuitry, the discharge circuit, the battery, and the capacitor are housed.

According to an embodiment of any paragraph(s) of this summary, the single continuous casing may have a single display that acts as the on/off interface for the wearable defibrillator.

According to an embodiment of any paragraph(s) of this summary, the single continuous casing may include a capacitance or mechanical switch configured to provide an on/off function for the wearable defibrillator.

According to an embodiment of any paragraph(s) of this summary, the wearable defibrillator may be at least one of waterproof or ruggedized.

According to an embodiment of any paragraph(s) of this summary, the wearable defibrillator may include a sensor that is configured to detect a size of an arresting person, wherein the wearable defibrillator is configured to automatically adjust a level of defibrillation based on the detected size.

According to an embodiment of any paragraph(s) of this summary, a distributed emergency defibrillator system includes a plurality of wearable defibrillators and at least one node configured to, in response to an input that a person is having a cardiac or pulmonary event, determine a location where the cardiac or pulmonary event is occurring based on location information associated with the input, communicate with a wireless network to determine at least one of mobile electronic devices associated with users who have access to the wearable defibrillator units, and send a notification to the at least one of the mobile electronic devices indicating that the cardiac or pulmonary event is occurring at the location.

According to still another aspect of the disclosure, a computer-implemented method includes receiving an input from a first mobile electronic device that corresponds to a cardiac or pulmonary event occurring in a person located within a proximity of the first mobile electronic device, accessing a wireless network that is in communication with the first mobile electronic device and second mobile electronic devices associated with users who have access to portable defibrillator units, determining a location of at least one of the second mobile electronic devices that is within a predetermined distance of the first mobile electronic device, and sending a notification to the at least one of the second mobile electronic devices indicating that the cardiac or pulmonary event is occurring.

According to an embodiment of any paragraph(s) of this summary, the method may include sending instructions to at least one of the at least one of the second mobile electronic devices or the first mobile device, the instructions pertaining to use of one of the portable defibrillator units.

According to an embodiment of any paragraph(s) of this summary, the method may include at least one of sending medical information for the person having the cardiac or pulmonary event to at least one of the at least one of the second mobile electronic devices or the first mobile electronic device or displaying the medical information on the first mobile electronic device.

According to an embodiment of any paragraph(s) of this summary, the method may include sending a secondary notification to at least one of third mobile electronic devices that are in communication with the wireless network and are associated with emergency contacts who are associated with the person having the cardiac or pulmonary event.

According to an embodiment of any paragraph(s) of this summary, the method may include sending an alert to an emergency central call station.

According to an embodiment of any paragraph(s) of this summary, the method may include outputting, by the one of the second mobile electronic devices, a unique sound or audio verbal signal that corresponds to a cardiac event or a pulmonary event.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The annexed drawings, which are not necessarily to scale, show various aspects of the disclosure.

DETAILED DESCRIPTION

The present application is directed towards defibrillator devices, systems, and methods. The defibrillator devices may be wearable and/or portable devices. The defibrillator system may implement wearable and/or portable defibrillator devices, or larger defibrillator devices, such as conventional defibrillators that are operable with the defibrillator system. The methods described herein include computer-implemented methods that may be carried out by one or more nodes that are connected to a network, such as a wireless network. Exemplary nodes include servers, sensors, and electronic devices, such as phones, computers, tablets, wearables, such as wrist watches, and so on. Any suitable hardware and/or software components may be used in conjunction with the principles described herein. This also applies to a witness of a cardiac event who has a wearable defibrillator and uses the wearable defibrillator without going through the computer system.

Figure 1:
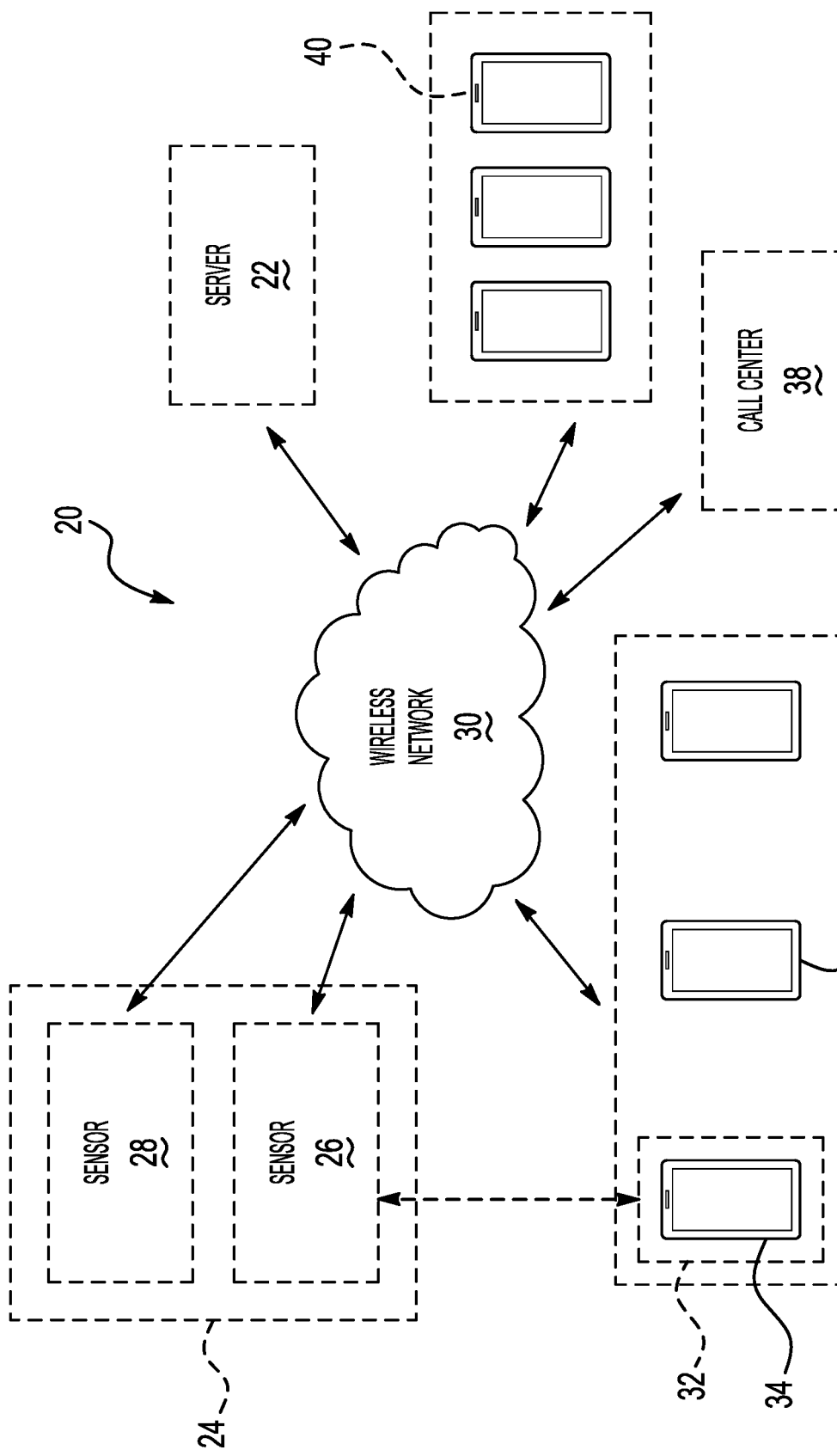
FIG. 1 shows a distributed defibrillator system according to an exemplary embodiment of the present application.

Referring first to FIG. 1, a distributed defibrillator system 20 is shown. The defibrillator system 20 enables a person with access to a wearable and/or portable defibrillator to reach a person who needs resuscitation in minimum time. People may not be able to defibrillate themselves. The defibrillator system 20 is configured to recognize that a cardiac and/or pulmonary event is occurring that requires defibrillation and resuscitation, and, if a person is wearing a defibrillator, to assist the person requiring defibrillation or notify someone else in close proximity to the unconscious person. The defibrillator system 20 may include a server 22.

Location information pertaining to the person having the cardiac or pulmonary event may be determined by any node that is connected to the network in the system, including the server, or a mobile device or wearable device. The node may include any suitable processor, and one or more computer-readable media storing instructions that are executable by the one or more processors to perform operations of the node. Each node may have a unique node identifier relative to other nodes connected to the network. The location information may be inputted verbally into a node if someone describes the location. Any node of the system 20 or the server 22 of the system 20 is configured to use the information to determine a first location 24 where a person having a cardiac or pulmonary event is located based on location information associated with an input. For example, a mobile device may be used to determine the first location 24 of the arrest or receive the location from another device in the system 20. The first location 24 where the person having the cardiac or pulmonary event is located may be a home, office, school, or other building. The first location 24 may be an outside location, or any detectable location where the person having the cardiac or pulmonary event, also referred to as an "arresting person," may be located.

The input corresponding to the person having the cardiac or pulmonary event may be any suitable input and may correspond to an output from any suitable sensor or electronic device. The location information associated with the input may be determined by the electronic device or by a sensor, such as by GPS integrated in the device. A person can witness the arrest and describe the location or give access to their phone location for location purposes. For example, the input may be received from at least one sensor 26 that is arranged in the first location 24. The sensor 26 may be an independent module that is arranged in the first location 24. Alternatively, the sensor 26 may be arranged in an electronic device associated with the arresting person or in a portable defibrillator unit in the first location 24. In an exemplary embodiment, the sensor 26 may be in a wearable defibrillator that is worn by the person having the cardiac or pulmonary event.

The sensor 26 may include one or more sensors that are arranged in the first location 24 or proximate the first location 24. For example, multiple sensors may be arranged around a home or the multiple sensors may include any combination of independent sensors, electronic device sensors, and defibrillator sensors. Any suitable sensor type may be used to generate the input for the defibrillator system 20. Exemplary sensors include a pO2 sensor, a pcO2 sensor, a movement transducer, an electrocardiogram transducer, a heart mechanical activity sensor, a heart electrical activity sensor, or combinations thereof. Many other sensor types may be used. More than one sensor may be used to provide redundancy for the defibrillator system 20, e.g., to confirm that a cardiac or pulmonary event is in fact occurring.

The sensor 26 may have any orientation and may be positioned relative to a bed, including under a bed. The sensor 26 may be built into a ceiling or other wall of a room. The sensor 26 may be integrated into the bed, a mattress, a pillow, an alarm clock, or in a wearable device of the arresting person, e.g., a necklace, watch, and so on. The sensor 26 may be configured to monitor a person sleeping, such that the system may be autonomous. For example, the sensor 26 may be integrated into an alarm clock such that the alarm clock may monitor a heart of the sleeping person. If the heart stops, the alarm clock sensor may automatically wirelessly send the signal to be received by a node or by the server 22 or send out an alarm as the input that the cardiac or pulmonary event is occurring. The alarm clock or other apparatus including a sensor may also be configured to determine if a person is arresting due to sleep apnea or another condition.

The sensor 26 may be configured to, via a wired or wireless connection, determine if the person's heart has stopped, is in ventricular fibrillation, or if the person stops breathing. The distributed defibrillator system 20 may be configured to notify a preset list of people, such as emergency contacts for the arresting person, and/or anyone in close proximity to the unconscious person, such as a neighbor or passerby that has a sensor, electronic device, wearable defibrillator, or other device that is part of the defibrillator system 20. A node of the system 20, e.g., a mobile device, or the server 22 may be configured to store the data pertaining to the appropriate people to contact. The defibrillator system 20 may be configured to send a signal or alarm to anyone in the first location 24, such as in the house or in a neighboring house. For example, the defibrillator system 20 may be configured to send a signal to another sensor 28 of the defibrillator system 20 located in the first location 24 or within a predetermined distance of the first location 24.

The sensors 26, 28 located in the vicinity of the arresting person may be used to determine the need for intervention, e.g., cardiopulmonary resuscitation or any other type of intervention. Accordingly, a node of the system 20 or the server 22 may be configured to analyze the data received from the sensors 26, 28 to determine what type of intervention is needed and perform an action that corresponds to the type of intervention, such as contact emergency personnel (emergency medical service (EMS) or 911 or other emergency system as may exist in other countries or locations) and/or contact a person who is able to defibrillate the person and/or determine that no action is needed and/or contact emergency contacts for the arresting person, such as family, friends, or neighbors.

In exemplary embodiments, the sensors 26, 28 may be independent of a defibrillator that is also located in the first location 24. In other exemplary embodiments, the sensors 26, 28 may be incorporated into the defibrillator located in the first location 24, so if someone has a cardiac arrest or stops breathing, the defibrillator acts as a node in the system 20 and automatically sends out a signal to another node or the server 22, which subsequently sends out a notification such as an alarm and/or an electronic signal to other nodes or devices such as mobile phones, pads, computers, and so on.

The defibrillator system 20 is configured to communicate via a wireless network 30 with which all of the devices associated with the defibrillator system 20 also communicate. The wireless network 30 may include any suitable communication protocol such as Bluetooth, cellular, Wi-Fi, and so on. In an exemplary embodiment, the defibrillator system 20 may be configured to increase the protocol area of coverage as necessary. For example, Bluetooth may be used for local communication, such as among sensors 26, 28 located in the first location 24, and if there is no response, e.g., a person receiving a signal, alarm, or other notification via the sensor 28 does not send an acknowledgement signal back to the node or the server 22 to confirm that the person will act and defibrillate the person having the cardiac or pulmonary event, Wi-Fi, cellular, or another protocol may be implemented to contact other people associated with the wireless network 30 who may be able to assist the arresting person. Since many people may be wearing the defibrillator all the time, including police, fireman, EMS personnel, and private citizens, the wearers may be close to an arresting someone that needs defibrillation and directly implement defibrillation without going through the network.

In addition to the situation in which the defibrillator system 20 sends a notification to the second sensor 28 located in the first location 24, or in an alternative embodiment in which there is only one sensor 26 in the first location 24, or in still another situation in which no response is received after the second sensor 28 is triggered, the defibrillator system 20 is configured to communicate with the wireless network 30 to determine a second location 32 of at least one mobile electronic device 34, 36 associated with users who have access to portable defibrillator units. The second location 32 is within a predetermined distance D of the first location 24. For example, the predetermined distance D may be preset by a user and based on mileage or time of travel for someone from the second location 32 to reach the person in the first location 24 after the person is notified of the cardiac or pulmonary event.

Having access to portable defibrillator units may mean that the person has their own portable defibrillator unit or they have access to a portable defibrillator unit, such as a portable defibrillator unit located at a predetermined location proximate the first location 24, or a defibrillator associated with the person having the cardiac or pulmonary event, such that the defibrillator is already at the first location 24. "Proximate" may be defined as being near enough to the arresting person so that the assisting person is able to reach the arresting person in time to perform a successful defibrillation. The person having the cardiac or pulmonary event may or may not have a defibrillator. A node of the system 20, e.g., a mobile device, or the server 22 of the defibrillator system 20 is configured to determine the pertinent information pertaining to access to a defibrillator in identifying the appropriate person to notify of the cardiac or pulmonary event.

For example, the node or the server 22 may be configured to store data pertaining to people who do not have defibrillators and people who do have a personal defibrillator, such that if the node or the server 22 receives an input from a person having a cardiac or pulmonary event that does not have a defibrillator, the node or the server 22 may only identify a person who has a defibrillator and is within proximity of the first location 24. Similarly, if the node or the server 22 receives an input from the arresting person who does have a defibrillator, the node or the server 22 may identify anybody who is within the proximity of the first location 24 and able to assist, regardless of whether the person has a defibrillator or not. In a distributed system, the person's own wireless device, such as a mobile phone, can provide the required information, such that a server 22 may not be necessary.

Any number of mobile electronic devices 34, 36, sensors, and defibrillators may be associated with the defibrillator system 20. As shown in FIG. 1, a first mobile electronic device 34 may be in the second location 32 while a second mobile electronic device 36 may not be within the second location 32, such that the person associated with the mobile electronic device 36 is not able to assist the person having the cardiac or pulmonary event in the first location 24. Accordingly, only the first mobile electronic device 34 may be identified and notified by another node or the server 22 of the cardiac or pulmonary event. However, if the second mobile electronic device 36 is associated with a designated emergency contact of the arresting person, the second mobile electronic device 36 may also be notified by the node or the server 22 that the cardiac or pulmonary event is occurring if desired by the arresting person.

After determining that the mobile electronic device 34 is in the second location 32 that is within the predetermined distance D of the first location 24, the defibrillator system 20 is configured to send a notification, such as a signal or an alarm, to the mobile electronic device 34 indicating that the cardiac or pulmonary event is occurring at the first location 24. Accordingly, in contrast to conventional defibrillator systems, the defibrillator system 20 is configured to send out a notification to anyone in the vicinity who is able to assist instead of a central call station or to an external control panel. The person who has access to a portable defibrillator unit can then act accordingly. Sending the notification directly to anyone in the vicinity saves time which is critical in cardiac or pulmonary situations.

The defibrillator system 20 may additionally or alternatively send a signal to a central call center 38 for an emergency response, e.g., "911" in the United States or EMS. In exemplary embodiments, the central call center 38 is in communication with the defibrillator system 20 through the wireless network 30. The server 22 may be located at the central call center 38 in other exemplary embodiments. Wireless network systems can also be used independently of a server as a distributed system to send information. Conventional call centers currently only determine which emergency medical service should respond and where to go. In contrast, in the defibrillator system 20, the call center 38 may be configured to locate people close to where the cardiac or pulmonary event is occurring via their cellular location and direct the person to the site of the emergency, rather than, or in addition to, sending emergency personnel. Other systems such as cellular GPS, GPS in a car, GPS in an alarm clock or home, or other independent systems may also be implemented with the defibrillator system 20.

The notification sent to the mobile electronic device 34 associated with the user in proximity of the first location 24, the sensor 28 located within the first location 24, and/or the call center 38 may include any suitable message, sound, and so on. The notification could be a text message or other notification associated with an application on the mobile electronic device. The notification may include specific medical information or special instructions corresponding to the person having the cardiac or pulmonary event. For example, the notification may include information regarding another condition of the arresting person for the assisting person to be aware of, such as deafness, diabetes, previous electrocardiograms, hip, leg, or other replacement body parts, allergies, and so on, or doctor information, a previous date of another cardiac or pulmonary events, and so on. Instructions for use may also be communicated through electronic device. An additional function of a second processor, such as a Bluetooth processor may be used to accomplish this.

The defibrillator system 20 may be configured to set off an alarm that has a unique sound and audible notification regarding the type of event occurring, e.g., whether the event is cardiac or pulmonary, and indicate the type of emergency that requires immediate action or the type of action that is required. The system may specify what the unique sound is or the unique sound may be preset by the system such that every user hears the same sound corresponding to the same event. The alarm may include audio verbiage, such as "cardiac arrest" or "pulmonary arrest," instead of or in addition to an audio signal. Accordingly, the person who is able to assist is notified immediately and able to quickly recognize what type of event is occurring and what type of action is required.

A node of the distributed system or the server 22 of the distributed system 20 may also be configured to store data pertaining to emergency contacts who are associated with the person located in the first location 24 that is having the cardiac or pulmonary event, but may not have access to a portable defibrillator. The emergency contacts may be located proximate the person having the cardiac or pulmonary event or remotely. For example, the emergency contacts may be family members or friends who have an interest in the health of the person having the cardiac or pulmonary event. The emergency contacts are also associated with secondary mobile electronic devices 40 other than the mobile electronic devices 34, 36 associated with the users who have access to the portable defibrillator units.

The server 22 or a node of the distributed system 20 is configured such that upon receiving the input corresponding to the cardiac or pulmonary event occurring, the defibrillator system 20 would send a secondary notification to at least one of the secondary mobile electronic devices 40 associated with the emergency contacts indicating that the cardiac or pulmonary event is occurring. The system 22 may or may not be configured to send location information. This notification may also include a unique message, sound, and so on, corresponding to the type of event occurring and the action that needs to be taken. The secondary notification may also include information pertaining to medical information for the person having the cardiac or pulmonary event, and information regarding who will be resuscitating the person and status updates. In other exemplary embodiments, the defibrillator system 20 may be able to track the location of the assisting person and provide location data to the emergency contact in real time such that the emergency contact knows that the arresting person is being assisted, and when the arresting person has been resuscitated. Once a person who can assist the arresting person is identified, tracking information of the person with defibrillator can be sent so others know how close they are.

In addition to, or alternatively to the stored data pertaining to the emergency contacts, the node or the server 22 may also be configured to store data pertaining to authorized users who are associated with the mobile electronic devices 34, 36 and who are authorized to access lock boxes containing portable defibrillator units. The lock boxes may be arranged near the location of the authorized user, i.e., at the second location 32, or near the first location 24 where the person having the cardiac or pulmonary event is. When the defibrillator system 20 sends the notification to the authorized user, and the authorized user does not have their own defibrillator, the notification may include an access or unlock code for one of the lock boxes such that the authorized user can retrieve the portable defibrillator unit prior to assisting the person having the cardiac or pulmonary event. The code may include any suitable combination of numbers, letters, and so on, that are able to be input into the locked device for unlocking the device.

For example, the stored data may include a list of authorized users who have undergone some sort of certification as to using defibrillators or other emergency resuscitation techniques. In another exemplary embodiment, sending the notification may also include sending instructions as to how to use the portable defibrillator unit. In still another embodiment, the unlock code sent to the assisting person may correspond to unlocking a portable defibrillator unit that is worn by the person having the cardiac or pulmonary event, such that the assisting person does not need to access a separate defibrillator and can proceed to go to the first location 24 to assist the arresting person.

Figure 2:
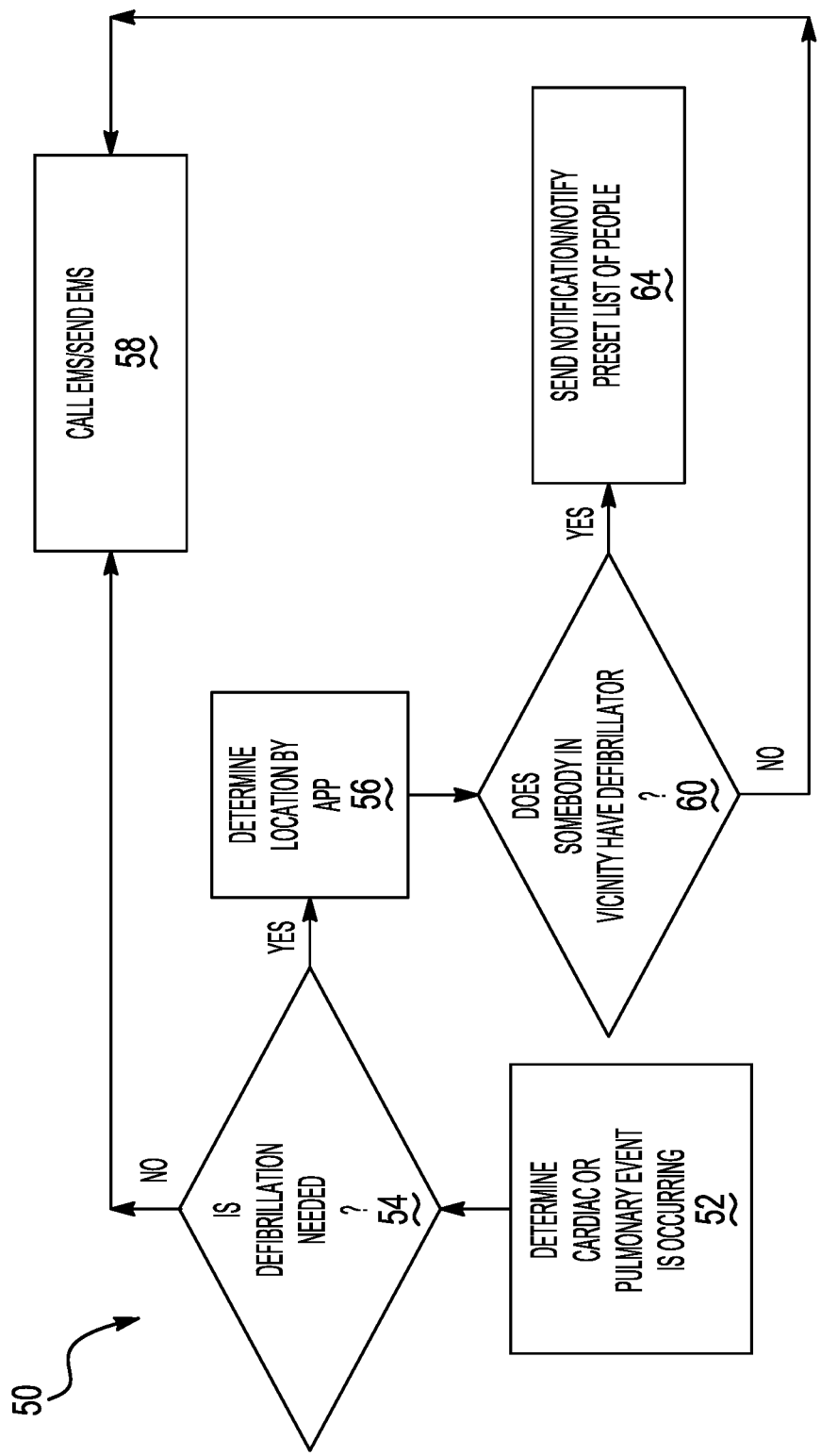
FIG. 2 shows a flowchart for an exemplary method of operation of the distributed system of FIG. 1.

Referring in addition to FIG. 2, an exemplary method 50 of operation for the defibrillator system 20 of FIG. 1 is shown. Step 52 of the method 50 includes determining that the cardiac or pulmonary event is occurring, such as via the sensor 26 located in the first location 24 where the person having the cardiac or pulmonary event is located. Step 54 of the method includes determining whether defibrillation is needed which may be performed by a node, e.g., mobile device, or the server 22 receiving and analyzing the input received from the sensor 26. If the data analyzed by the node or the server 22, or by independent methods such as witnesses of the event indicate that defibrillation is needed, step 56 of the method 50 includes determining the location of the person having the cardiac or pulmonary event and/or calling a call center 38, i.e., emergency response, such as EMS/911. If the node or the server 22 determines that defibrillation is not needed, such as if the problem is a diabetic hypoglycemic or hyperglycemic issue, another action may be taken and/or step 58 may occur in which the emergency response center is called and emergency response personnel may be dispatched to the first location 24.

Step 56 may be performed by the node or by the server 22, such as via an application for an electronic mobile device and/or via the node or the server 22. The server 22 may be arranged at the call center 38 in exemplary embodiments. After determining the location of the person having the cardiac or pulmonary event, step 60 may occur. Step 60 includes determining if somebody in the vicinity of the arrested person has a defibrillator or access to a defibrillator, such as access to a defibrillator located proximate the person having the cardiac or pulmonary event. For example, the defibrillator may be a personal wearable defibrillator for the arresting person. If there is somebody located in the vicinity that is able to assist with defibrillation, step 64 occurs in which the node or the server 22 is configured to send a notification to the electronic devices associated with any person who is able to assist with defibrillation and/or send notifications to emergency contacts of the person having the cardiac or pulmonary event as previously described. For example, the notification may include sending access information for the personal wearable defibrillator of the arresting person to the person who is able to assist. After the person receives the notification, the person may defibrillate the arresting person.

If the node or the server 22 is unable to identify a person who is able to assist the arresting person in step 60, step 58 may occur in which the node or the server 22 may be configured to call the call center such that EMS personnel may be sent to the arresting person. If the node or the server 22 determines that emergency response is needed, which may be based on the data received and analyzed by the node or the server 22 pertaining to the health and current condition of the arresting person and/or a preset preference of the arresting person, step 58 may occur.

Figure 3A:
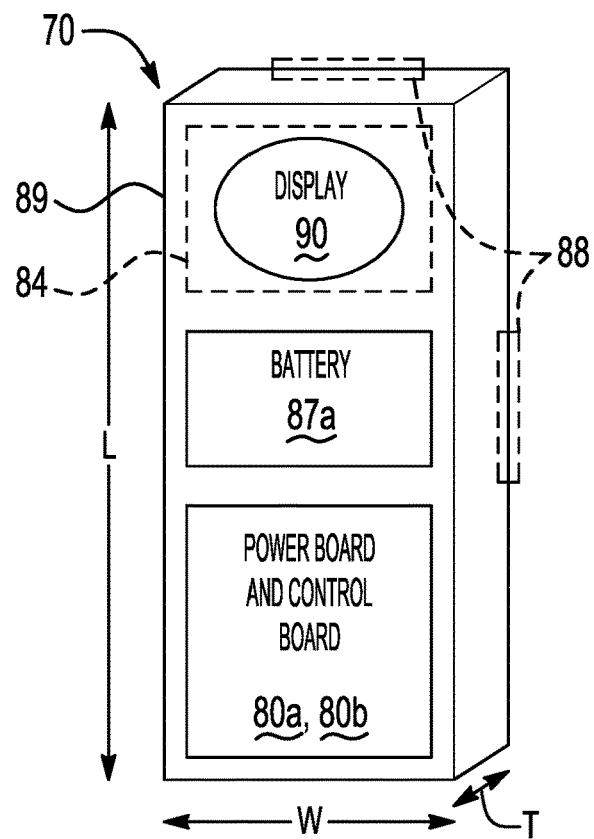
FIG. 3A shows a schematic drawing of a wearable defibrillator according to an exemplary embodiment of the present application.
Figure 3B:
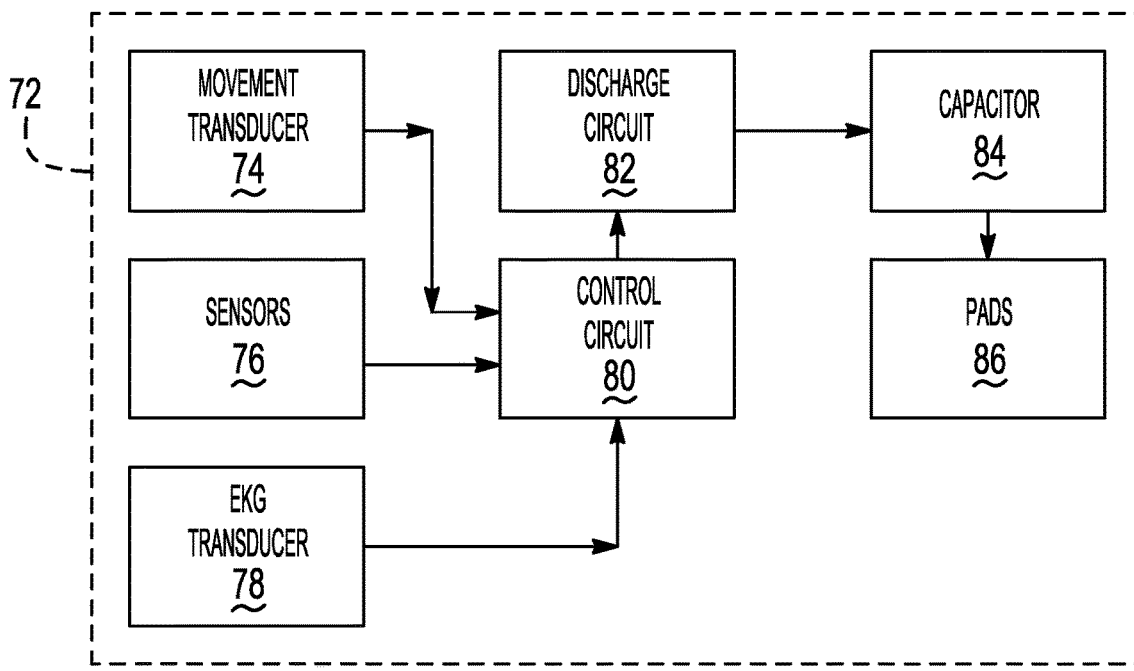
FIG. 3B shows a control circuit for the wearable defibrillator of FIG. 3*a*.

Referring now to FIGS. 3A and 3B, an exemplary wearable defibrillator 70 and the corresponding electronics 72 are shown. The wearable defibrillator 70 may be suitable for use in the defibrillator system 20 of FIG. 1, and any number of wearable defibrillators 70 may be used in the defibrillator system 20. For example, the person having the cardiac or pulmonary event, or any of the people associated with the mobile electronic devices 34, 36 may wear a wearable defibrillator 70. In contrast to some conventional one-time use defibrillators or for use on one person, the wearable defibrillator 70 is configured for repeatable use and on different people, such as during a military situation or terrorist attack when multiple people require defibrillation.

The wearable defibrillator 70 may be portable and have an overall size that is comparable to the size of a mobile phone. In an exemplary embodiment, the wearable defibrillator 70 may have a thickness T that is between 0.75 and 1.25 inches, a length L that is between 6.0 and 7.0 inches, and a width W that is between 3.0 and 3.5 inches. Many other dimensions are possible and the wearable defibrillator 70 may be sized up or down. In contrast to conventional defibrillators which are larger, the components contained in the wearable defibrillator 70 are both manufactured and arranged to enable minimizing the size of the wearable defibrillator 70. Thus, the wearable defibrillator 70 is easily portable and comfortable for the wearer.

The electronics of the wearable defibrillator 70 includes one or more sensors, such as a motion, accelerometer sensor or movement transducer 74, $pO_2$ and/or $pCO_2$ sensors 76, and an electrocardiogram (EKG) transducer 78 that are configured to communicate with a control circuit 80. The sensors may correspond to any of the sensors described with respect to FIG. 1, such that the sensors are configured to provide an input to the node or the server 22 or control circuit 80 regarding a cardiac or pulmonary event occurring. Many other types of sensors may be used.

The sensors may be mounted close to the wearer's heart, such as in a pocket of clothing, to sense EKG or movement if a cardiopulmonary or other negative event occurs. The movement transducer 74 may be used to detect the motion of the chest and/or to detect if the heart is pumping. Due to the pattern of the chest movement, the movement transducer 74 may detect if there is a fatal event or not. The movement transducer 74 may operate in conjunction with the EKG transducer 78. The control circuit 80 of the wearable defibrillator 70 may be configured to receive and analyze the data from the sensors to determine whether defibrillation is required, and/or to communicate with the node or the server 22 if somebody should be notified to assist the arresting person. The additional sensor in the defibrillator 70 improves determination that a person should be defibrillated.

In other exemplary embodiments, the sensors 76 may include an accelerometer that is built into the wearable defibrillator 70, such as in the pads or as a separate attachment configured to operate in conjunction with the wearable defibrillator 70 such that, when placed on unconscious person, the accelerometer is used to determine movement due to the heart or breathing of the wearer. A pattern, such as ventricular fibrillation, may be determined and the electronics of the wearable defibrillator 70 may be configured to determine that action is required. The wearable defibrillator 70 may be configured to turn itself on if the situation warrants based on detected data from the sensor.

The control circuit 80 is configured to communicate with a discharge circuit 82 and a capacitor 84 that is connected to electrode pads 86. The electrode pads 86 may include separable pads that each have electrodes. The discharge circuit 82 is configured to release a voltage from a capacitor of the wearable defibrillator 70 to at least one of the electrodes.

In another exemplary embodiment, a radio-frequency identification (RFID) device is built into the defibrillator to aid in manufacturing and as a non-volatile storage of information in case of catastrophic failure of defibrillator.

In still another exemplary embodiment, the sensors 76 may include a sensor that is configured to automatically detect the size of the arresting person and set a level of defibrillation for the defibrillator 70 based on the detected size of the arresting person since the defibrillation characteristics may be different for, for example, in children and adults. Detection can be through the accelerometer, impedance sensed by the leads and/or electrode pads, and other techniques.

Figure 3C:
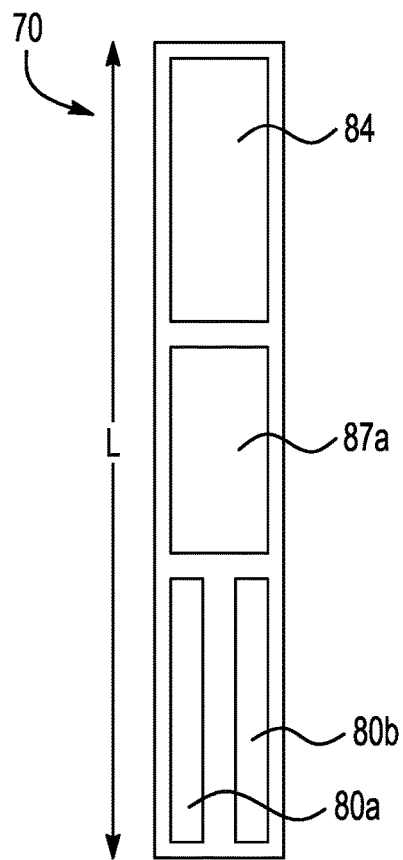
FIG. 3C shows a side view of the wearable defibrillator of FIG. 3*a*.
Figure 3D:
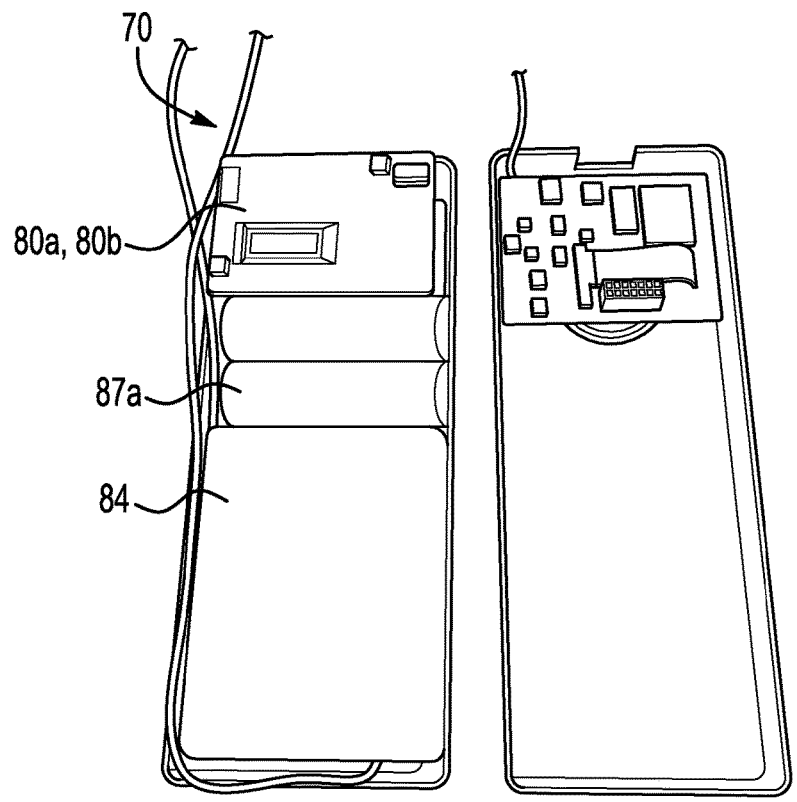
FIG. 3D shows an interior of the wearable defibrillator of FIG. 3*a*.

Referring in addition to FIGS. 3C and 3D, most or all of the major electronic components of the wearable defibrillator 70 may be placed next to each other to minimize the depth of the wearable defibrillator 70, i.e., maintain a low profile. For example, the capacitor 84, battery or batteries 87a, and other electronics, such as the power circuitry 80a and control circuitry 80b, are arranged in a serial arrangement with stacked discharge and control circuitry which makes the wearable defibrillator 70 more wearable in contrast to conventional larger defibrillators. The power circuitry 80a and control circuitry 80b are stacked, meaning they are adjacent to each other in a direction that is normal relative to the length L of the wearable defibrillator 70. The circuitry 80a, 80b are then arranged in serial relation with the battery 87a and the capacitor 84 along the length L of the wearable defibrillator 70.

The wearable defibrillator 70 may be worn in multiple personal environments, e.g., on a belt, pants, dress, in or on a pocket, and so on, in an efficient and secure manner. "Wearable" may mean that the device is small enough to be conveniently worn. The shape of the wearable defibrillator 70 is substantially planar or flat, such that it may be mounted on a belt or put it in a pocket in a way that has minimal interference with the wearer. In contrast, conventional defibrillators are luggable and not easily worn or worn at all. The wearable defibrillator 70 may also include straps for mounting to arms or legs. A mounting device 88 is schematically shown in FIG. 3a and the mounting device 88 may be arranged anywhere on the wearable defibrillator 70, such as on the sides, back side, front side, top, or bottom of the wearable defibrillator 70. Multiple mounting devices 88 may be provided. The mounting device 88 may include a strap, hook, clip, fastener, and so on. The mounting device 88 may be modular in that the wearable defibrillator 70 may have a connection arranged to receive a strap, clip, or other mounting accessories depending on the preference of the wearer. The connection may include any suitable latching mechanism.

The mounting device 88 may be configured for mounting only the electrode pads 86 to the wearer, the defibrillator 70, or both. In still another exemplary embodiment, the mounting device 88 may include a locking mechanism or disconnectable portion that requires a code for disconnecting the wearable defibrillator 70 from the mounting device 88, such that the mounting device 88 may remain attached to the wearer. The locking mechanism may be a mechanical lock or an electronic lock. Using the code for unlocking the mounting device 88 may limit unauthorized use of the wearable defibrillator 70. For example, if the wearable defibrillator 70 is used in the defibrillator system 20, the node or the server 22 may be configured to send an access code to unlock the lock and/or instructions for operating the wearable defibrillator 70 to the mobile electronic devices 34, 36 associated with the authorized defibrillator users. Alternatively, the node or the server 22 may be configured to automatically unlock the lock.

The electrode pads 86 may be mounted in the front, to the sides, top or bottom and/or behind the wearable defibrillator 70 using any suitable mount. In exemplary embodiments, the electrode pads 86 may be inside part of a belt or closest to the body of the wearer. The wearable defibrillator 70 may include an inverted "U" clip that is configured to store the electrode pads 86 inside the pants, such as between the inner surface of the pants and body/shirt, like a pocket. Accordingly, the external exposure and depth of the defibrillator may be minimized. The electrode pads 86 are formed of any suitable thin and flexible material for comfort of the wearer.

The wearable defibrillator 70 may have a single and continuous case 89 that is formed to be buttonless, such that the case 89 is ruggedized and waterproof. The case 89 is configured to house the control circuit 80, the capacitor 84, and the discharge and power circuit 80, 82. The case 89 may be formed of any suitable waterproof material, and have any suitable shape. For example, the case 89 may be rectangular, but many other shapes are possible. The wearable defibrillator 70 may include a single display 90 for turning on and off the wearable defibrillator 70. All of the operations of the wearable defibrillator 70 may be performed through the one display 90, such that there are no separate on or off or other defibrillator buttons, which enables the case 89 to be waterproof and prevent dirt or other debris from entering the wearable defibrillator 70. In other exemplary embodiments, the defibrillator 70 may include a separate on or off button or other mechanical switch.

As further described below, charging may be performed wirelessly such that there are no connectors in the case 89 which further enables the case 89 to be waterproof. The electronics may be completely enclosed by the case 89. Accordingly, the configuration of the wearable defibrillator 70 enables the wearable defibrillator 70 for use in rugged applications, such as military, construction, industrial, or any other applications performed in outdoor environments.

Figure 4:
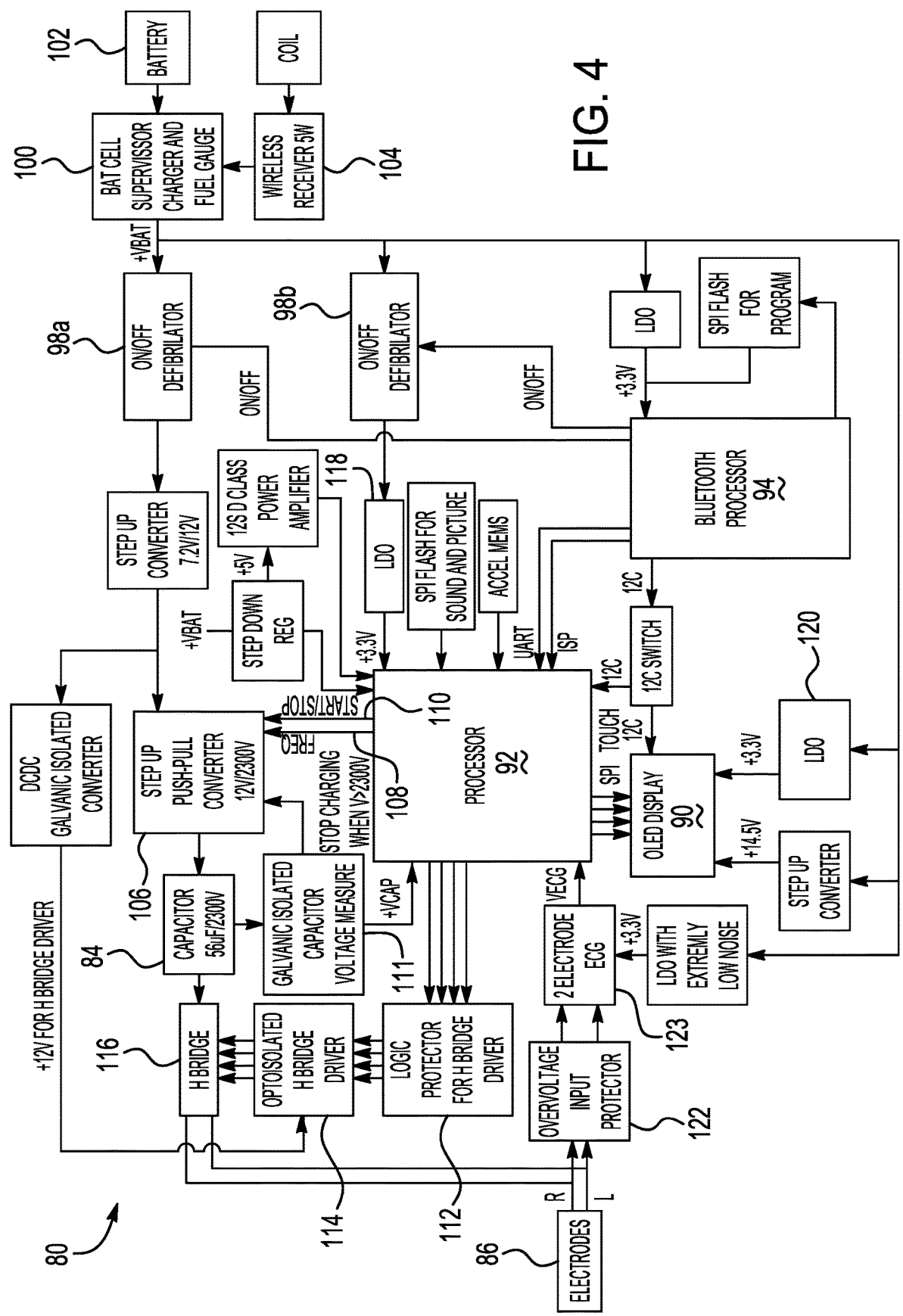
FIG. 4 shows a control circuit for the wearable defibrillator of FIG. 3*a* according to an exemplary embodiment of the present application.

Referring in addition to FIG. 4, an exemplary embodiment of the control circuit 80 for the wearable defibrillator 70 of FIG. 3a is shown. The control circuit 80 includes a main processor 92 and a Bluetooth (or other communication protocol) processor 94 that is communicatively coupled with the main processor 92. This enables a wireless connection with the wearable defibrillator 70 and wireless electronic devices, such as phones, pads, computers, and so on, such as in the defibrillator system 20 of FIG. 1. Many different communication protocols may be possible. The communication protocol, e.g., Bluetooth, may also be used to locate the wearable defibrillator 70, in a "Find Me" function on an electronic mobile device. This enables people to locate the wearable defibrillator 70 if they are unable to easily do so, such as after a long period of time in which the wearable defibrillator 70 is not used.

The Bluetooth interface may be in a sleep mode most of the time and awakes when the display 90 is touched, or in response to the detection of a cardiac or pulmonary event occurring in a person by a sensor. The control circuit 80 includes "On/Off" modules 98a, 98b that are in communication with the Bluetooth processor 94 such that the Bluetooth processor 94 is able to communicate with the On/Off modules 98a, 98b to turn the wearable defibrillator 70 on and turn the defibrillation circuit on. For example, the On/Off module 98a may be configured to turn on the defibrillation circuit and the On/Off module 98b may be configured to turn on the defibrillator 70. The On/Off module 98 may not be mechanical or may be mechanical. The On/Off switch may be switched on through the display. By using two processors, the On/Off can be determined by a secondary processor, such as the Bluetooth interface in sleep mode which uses minimum power. The Bluetooth processor 94 is also used for communication to other mobile devices in that the display 90 acts as the on/off interface for the wearable defibrillator 70. The screen of the display 90 may be a light-emitting diode (LED) display, such as an organic (OLED) display, or other type of display, and acts as the user interface for the wearable defibrillator 70. The software may be updated by turning the Bluetooth processor 94 on and sending updates wirelessly to the wearable defibrillator 70. The software may be otherwise updated instead of or in addition to using Bluetooth.

The control circuit 80 further includes a battery control unit 100 that is configured to control charging the capacitor 84 for the wearable defibrillator 70. Any suitable battery 102 may be used and the battery 102 may be rechargeable. The capacitor 84 may be configured to be charged at a maximum rate until the capacitor 84 is nearly or at full charge. When the capacitor 84 reaches nearly full charge, charging of the capacitor 84 may then occur at a decreased rate that is controlled by the battery control unit 100. The battery control unit 100 acts as a self-testing module for the wearable defibrillator 70 and is configured to also monitor the strength of the battery 102 such that the wearable defibrillator 70 can notify the user if the battery 102 is low. The battery control unit 100 is also in communication with a wireless receiver 104 of the control circuit 80 and the On/Off module 98a for powering the capacitor of the wearable defibrillator 70.

The control circuit 80 further includes various converters. In enabling the wearable defibrillator 70 to be compact, the transformer core in the step up push-pull converter 106, which is communicatively coupled between the battery 102 and the capacitor 84, is configured to be very small. For example, conventional small defibrillators may be approximately 50 to 52 cubic inches, whereas the defibrillator 70 may be approximately 20 to 22 cubic inches. The step up push-pull converter 106 is powered up to the saturation point of the transformer core and is controlled by frequency and amplitude start/stop lines 108, 110 from the main processor 92. The capacitor charging loop further includes a capacitor voltage measure 111 arranged between the capacitor 84 and the main processor 92. The arrangement of the capacitor charging loop enables both a small form factor of the wearable defibrillator 70 and rapid charging of the capacitor 84 between shocks by the electrode pads 86.

For example, the charging time may be between eight and 10 seconds in contrast to an average 30 seconds for some conventional defibrillators. Accordingly, the time between shocks is reduced. Moreover, in conventional sized defibrillator systems where space and weight are not considered to be an issue, the capacitor charging time may begin when the defibrillation is turned on. In contrast, in the wearable defibrillator 70, the control circuit 80 is configured to charge the capacitor 84 when it is turned on, and, because of the rapid charge time, also immediately after the time of required defibrillation. As soon as the defibrillator control circuit 80 determines a charge is necessary, it begins charging which provides improved safety as compared with having the charge exist when charging is not needed.

Conventional defibrillator units charge to approximately 2300 volts by using 2300 volts. As the difference between the source and desired voltage get closer to the final voltage the charging becomes slower due to less current. In the defibrillator 70, charging occurs at approximately 1000 volts above the desired voltage such that 2300 volts can be reached quicker. Precise measuring and slow charging is used as the voltage approaches 2300 volts, but the charging is faster as compared when charging occurs from a 2300 volt source. Frequency of the converter 106 is controlled and the transformer is very small. A variable resonant frequency of around 50 kilohertz is used. The frequency begins at a frequency less than 50 kilohertz which results in a higher saturation and maximum efficiency. When near saturation, close to the desired capacitor voltage, the frequency is increased. As the frequency is increased, out of saturation, efficiency is decreased and charging is decreased but only close to the point of stopping charging. If more power is required, operation at near saturation core occurs and the operation is stopped close to saturation. The saturation changes with increased frequency since as frequency increases, saturation decreases. In contrast, conventional defibrillators operate below saturation and operate at a fixed frequency. The maximum allowed point in the defibrillator 70 is used by changing frequency and using maximum saturation in the defibrillator 70 enables improved efficiency as compared with conventional defibrillators.

The control circuit 80 further includes a logic protector module 112, i.e., a logic protector for the H-bridge driver of the electrode pads 86. If there is a failure in the software, the logic protector module 112 is configured to protect the firing of the wearable defibrillator 70 via an isolated bridge driver 114 configured to isolate the bridge 116 communicatively coupled between the capacitor 84 and the electrode pads 86, such that the capacitor 84 is prevented from connection with the electrode pads 86. The logic protector module 112 may be configured to prevent operation of the electrode pads 86 if there is a wrong command from the main processor 92 or a bad update in the software. This provides double protection in that the hardware is configured to protect against any software errors.

The control circuit 80 may include any other suitable electronic components. Low-dropout regulators (LDOs)

118, 120 may be provided to regulate output voltages from a higher-voltage input. For example, LDOs 118, 120 may be arranged between the On/Off module 98 and the main processor 92, and between the Bluetooth processor 94 and the display 90. Further circuit protection may be provided by an overvoltage input protector 122 arranged between the electrode pads 86 and the two electrode EKG (EKC) 123 that is communicated to the main processor 92. Power amplifiers, switches, micro electro mechanical system (MEMS) accelerometers, and various other regulators and converters may also be arranged in the control circuit 80. The arrangement and connections of all of the components in the control circuit 80 are provided to minimize the overall size of the wearable defibrillator 70.

Figure 5:
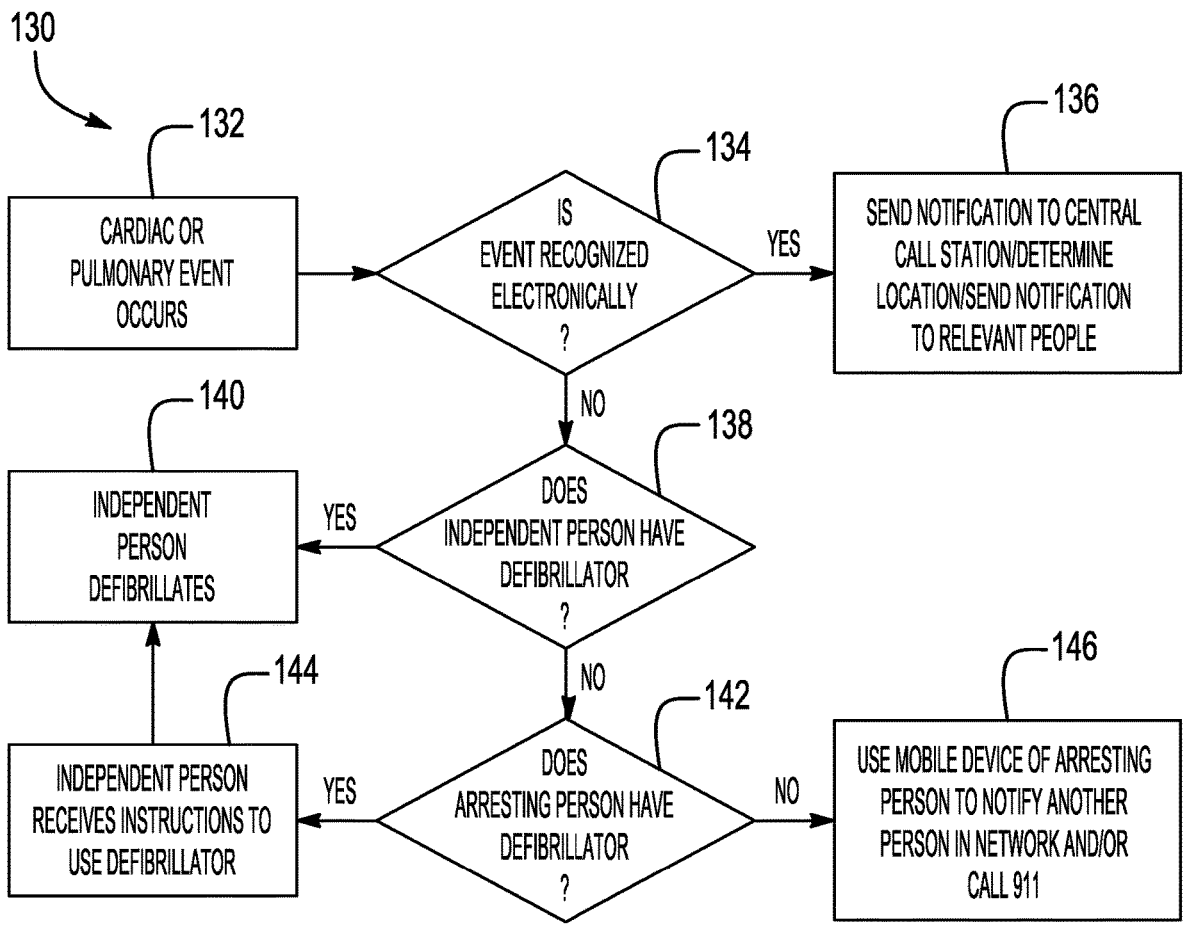
FIG. 5 shows a flowchart for an exemplary method of operation of a computer-implemented method for the distributed defibrillator system of FIG. 1.

Referring now to FIG. 5, still another aspect of the present application is an application for mobile devices, e.g., a computer-implemented method 130. The application may be used in conjunction with the defibrillator system 20, any node or server 22 and distributed system 20, and network 30 of FIG. 1. Step 132 of the method 130 includes detecting that a cardiac or pulmonary event occurs in a person. If an event does not occur, the application may be configured to monitor the person such as via a sensor as previously described. Step 132 includes an independent person witnessing the event and providing an input to a mobile device through the application, such that anybody with the application can be notified.

After the cardiac or pulmonary event 132 occurs, step 134 of the method 130 includes determining whether the event is recognized electronically, such as by the sensor, which may be independent, arranged in a mobile electronic device, or arranged in a wearable defibrillator, such as the wearable defibrillator 70 of FIG. 3a. In other exemplary embodiments, the detection may be provided from a worn device, such as a necklace, watch, jewelry, and so on, or from persons recognizing someone collapses.

If the cardiac or pulmonary event is automatically detected, step 136 may occur in which the application sends a notification to a central call station and anyone with the mobile device application and a defibrillator. The central call station is configured to determine the location of the arresting person and send EMS and/or notify the emergency contacts for the arresting person. Alternatively, step 132 may include an independent bystander witnessing a cardiac or pulmonary event occurring and have the application on their electronic mobile device. The independent person is able to provide an input into the electronic mobile device, or another wearable device, such as push a button, to trigger the application to send a notification to a central call station (emergency response or 911) and/or anyone else who has the application via Bluetooth, cellular or any other communication protocol.

The application may be configured to activate a unique sounding alarm in response to receiving an input from the independent person. Different emergency situations, e.g., whether the event is cardiac or pulmonary, may have unique alarms or voice verbiage stating the problem. The application enables anyone with the application who sees someone in need of help uses their own electronic mobile device, independent of the person in need, to notify everyone else who has the application and is wearing a defibrillator that is in reasonable proximity through an appropriate communication protocol that their services are needed and where they are needed.

The application may be configured to be activated by the independent person without logging into the phone of the arresting person. The application may include an emergency notification that is available to anyone when the phone turns on with a message that says: "Push this button in case of emergency". The emergency notification may be available on the mobile devices of both the independent person and the arresting person. Accordingly, the application network is activated and may send a notification to anyone with the application, and immediately provides instructions on how to use the defibrillator if the arresting person has a defibrillator or the independent person has access to a portable defibrillator or sends a signal to other independent persons with the application in the vicinity.

The application may incorporate a sensor or detection device to determine if a person is having a cardiac or pulmonary event, such that a communication add-on device may be provided with the application and the sensor. Mobile phones may be modified or detection hardware may be added on to existing mobile phones to wirelessly determine if a heart of a user stops or if the breathing stops. Either an application downloaded onto the mobile device may be activated to send out a notification or signal, or a communication add-on device may be configured to send out the notification. The location of an arresting person may be specified by the GPS phone location or by a defibrillator device or sensor worn by the arresting person.

In the event that an independent person using the application witnesses the cardiac or pulmonary event occurring, the application may be used to further question the independent person such as to determine whether the independent person has a defibrillator in step 138 of the method 130. If the independent person has a defibrillator, the independent person may indicate this in the application and proceed to step 140 in which the independent person defibrillates the arresting person. The application may be configured to provide status updates and/or location tracking of the independent person to other users so that others are made aware that the arresting person is being attended to and when the arresting person is resuscitated.

Step 140 may include the application simultaneously contacting the central call center or emergency response (911) while the independent person defibrillates the arresting person and/or notifying emergency contacts for the arresting person. The application may be configured to automatically notify the desired people and/or contact emergency response per a preset condition set by the arresting person.

If the independent person does not have a defibrillator, the application may inquire as to whether the arresting person has a defibrillator in step 142 of the method 130. This information may be determined by the application using stored data hosted on a server or in a node of a distributed system pertaining to users of the application. If the arresting person has a defibrillator, step 144 of the method 130 occurs in which the independent person receives instructions through the application or through the defibrillator or through the defibrillator communicating to an independent person's mobile device such as using Bluetooth built into the defibrillator regarding how to use the defibrillator and/or other medical information pertaining to the arresting person. The instructions may also include an unlock/access code if the defibrillator of the arresting person has a locking mechanism for access to prevent unauthorized use. Step 140 of the method then occurs and the independent person may defibrillate the arresting person. If the arresting person does not have a defibrillator in step 142, step 146 may occur in which the electronic mobile device is used to notify another person in the network and/or call 911.

Figure 6:
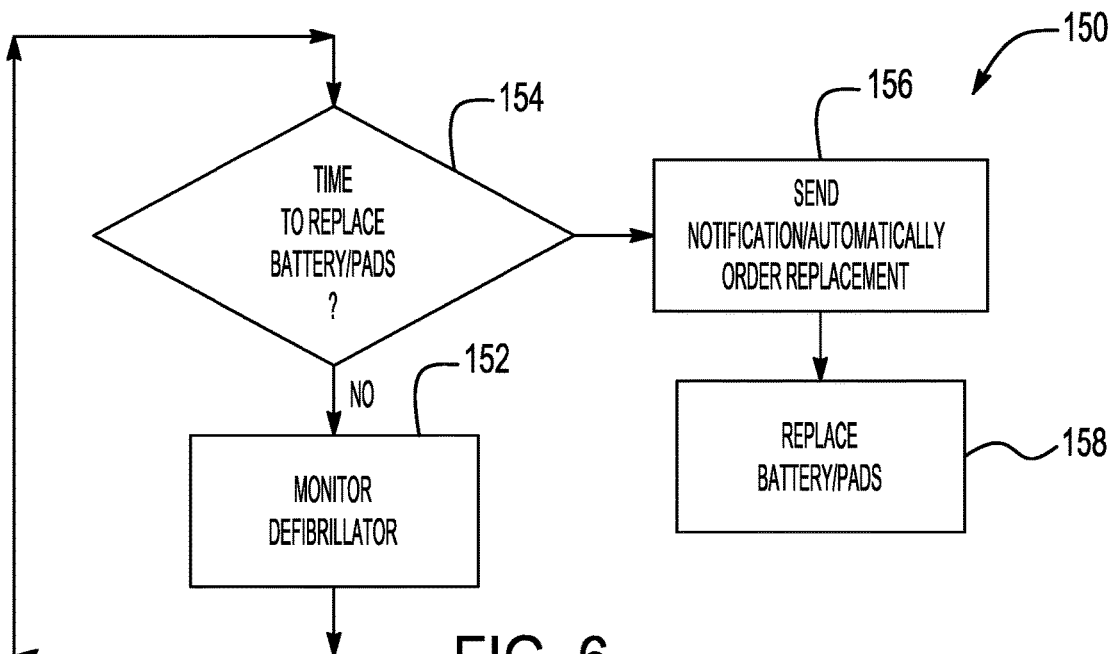
FIG. 6 shows a flowchart for another exemplary method of operation of a computer-implemented method for the distributed defibrillator system of FIG. 1.

Referring in addition to FIG. 6, the application may also be able to provide a monitoring function for a wearable defibrillator in that the application may be in communication with the wearable defibrillator via any suitable communication protocol. The application may notify the owner of the wearable defibrillator of a time to replace the battery and/or when to replace the pads, based on predetermined data regarding the lifetime of the pads and normal wear. The application may be able to determine wear based on a number of uses of the defibrillator tracked by the application. The defibrillator is monitored by the application at step 152 until the application determines that it is time to replace the battery and/or pads at step 154. If the application determines that it is time to replace the battery and/or pads, the application may send a notification to the user and/or automatically send an order to buy a new battery and/or pads in Step 156. Step 158 then occurs in which the battery and/or pads are replaced. Potential malfunction of the defibrillator may also be monitored.

The application may be configured to provide other data to the user regarding the electronics in the user's own wearable defibrillator. In an exemplary embodiment, the application may also be able to determine that the arresting person's defibrillator has a low battery such that the application will identify and notify only independent people who have their own defibrillator. In still other exemplary embodiments, the application may provide statistics regarding defibrillation activity in the network, such as how many people are on the network, how many defibrillations have occurred in a certain region, and so on.

Various techniques described herein may take the form of program code (i.e., instructions) embodied in tangible media, such as floppy diskettes, compact disc-read-only memory (CD-ROMs), digital versatile disc (DVD), hard drives, non-transitory computer readable storage medium, or any other machine-readable storage medium. When the program code is loaded into and executed by a machine, such as a computer, the machine becomes an apparatus for practicing the various techniques. Circuitry may include hardware, firmware, program code, executable code, computer instructions, and/or software. A non-transitory computer readable storage medium may be a computer readable storage medium that does not include signal. In the case of program code execution on programmable computers, the computing device may include a processor, a storage medium readable by the processor (including volatile and non-volatile memory and/or storage elements), at least one input device, and at least one output device.

The volatile and non-volatile memory and/or storage elements may be a random-access memory (RAM), erasable programmable read only memory (EPROM), flash drive, optical drive, magnetic hard drive, solid state drive, or other medium for storing electronic data. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, and so on), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A defibrillator comprising:
    a capacitor;
    a battery;
    control circuitry that includes one or more power converters;
    separable pads having electrodes; and
    a discharge circuit electrically coupled to the control circuitry and configured to release a voltage from the capacitor to at least one of the electrodes;
    a single continuous casing, wherein all circuitry, including the control circuitry, the discharge circuit, and any other circuit, of the wearable defibrillator except the separable pads having the electrodes and any wiring associated thereto is housed in the single continuous casing,
    wherein the defibrillator has a length that is a largest dimension of the defibrillator, a width that is the second largest dimension of the defibrillator, and a depth that is the third largest dimension of the defibrillator, wherein the capacitor, the battery, and the control circuitry are disposed along the length of the defibrillator such that the capacitor and the battery do not overlap any circuitry along the depth of the defibrillator, and each of the capacitor, the battery, and the control circuitry do not overlap along the width of the defibrillator.

2. The defibrillator according to claim 1 further comprising a disconnectable mount for mounting the defibrillator to a person.

3. The defibrillator according to claim 1 further comprising a disconnectable mount for mounting the separable pads to a person.

4. The defibrillator according to claim 1 further comprising a self-test module, wherein the self-test module monitors battery strength and functionality of the defibrillator.

5. The defibrillator according to claim 1, wherein the single continuous casing includes a capacitance or mechanical switch configured to provide an on/off function for the defibrillator.

6. The defibrillator according to claim 1, wherein the defibrillator is at least one of waterproof or ruggedized.

7. The defibrillator according to claim 1 wherein the control circuitry is disposed adjacent the control circuitry in a direction normal to the length of the defibrillator.

8. A defibrillator comprising:
    a capacitor;
    a battery;
    control circuitry that includes one or more power converters;
    separable pads having electrodes;

a discharge circuit electrically coupled to the control circuitry and configured to release a voltage from the capacitor to at least one of the electrodes, wherein the capacitor is a rechargeable capacitor and/or is configured to be charged at a maximum rate until the capacitor is nearly at full charge at which the capacitor is then charged at a decreased rate, wherein the defibrillator has a length that is a largest dimension of the defibrillator, a width that is the second largest dimension of the defibrillator, and a depth that is the third largest dimension of the defibrillator, wherein the capacitor, the battery, and the control circuitry are disposed along the length of the defibrillator such that the capacitor and the battery do not overlap any circuitry along the depth of the defibrillator, and each of the capacitor, the battery, and the control circuitry do not overlap along the width of the defibrillator.

9. A defibrillator comprising:

a capacitor;

a battery;

control circuitry that includes one or more power converters;

separable pads having electrodes;

a discharge circuit electrically coupled to the control circuitry and configured to release a voltage from the capacitor to at least one of the electrodes; and a sensor that has an output, wherein the defibrillator is configured to automatically adjust a level of defibrillation based on the output of the sensor, wherein the sensor is one or more of a pO2 sensor, a pCO2 sensor, a movement transducer, an electrocardiogram transducer, a heart mechanical activity sensor, or a heart electrical activity sensor, wherein the defibrillator has a length that is a largest dimension of the defibrillator, a width that is the second largest dimension of the defibrillator, and a depth that is the third largest dimension of the defibrillator, wherein the capacitor, the battery, and the control circuitry are disposed along the length of the defibrillator such that the capacitor and the battery do not overlap any circuitry along the depth of the defibrillator, and each of the capacitor, the battery, and the control circuitry do not overlap along the width of the defibrillator.

10. A distributed emergency defibrillator system comprising:

a plurality of defibrillators according to claim 1; and at least one node independent from the defibrillators and configured to, in response to an input that a person is having a cardiac or pulmonary event:

determine a location where the cardiac or pulmonary event is occurring based on location information associated with the input;

communicate with a wireless network to determine at least one of mobile electronic devices associated with users who have access to the defibrillators; and send a notification to the at least one of the mobile electronic devices indicating that the cardiac or pulmonary event is occurring at the location.

11. A defibrillator comprising:

a capacitor;

a battery;

control circuitry that includes one or more power converters;

separable electrode pads having electrodes;

a discharge circuit electrically coupled to the control circuitry and configured to release a voltage from the capacitor to at least one of the electrode pads via leads, wherein impedance is sensed by the leads and/or electrode pads, wherein the defibrillator has a length that is a largest dimension of the defibrillator, a width that is the second largest dimension of the defibrillator, and a depth that is the third largest dimension of the defibrillator, wherein the capacitor, the battery, and the control circuitry are disposed along the length of the defibrillator such that the capacitor and the battery do not overlap any circuitry along the depth of the defibrillator, and each of the capacitor, the battery, and the control circuitry do not overlap along the width of the defibrillator.

* * * * *